US00PP21896P2

(12) United States Plant Patent
Pieters

(10) Patent No.: US PP21,896 P2
(45) Date of Patent: May 3, 2011

(54) ***CHRYSANTHEMUM* PLANT NAMED 'MEFISTO PURPLE'**

(50) Latin Name: *Chrysanthemum×morifolium*
Varietal Denomination: Mefisto Purple

(75) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 12/653,951

(22) Filed: Dec. 18, 2009

(51) Int. Cl.
*A01H 5/00* (2006.01)

(52) U.S. Cl. ..... Plt./287

(58) Field of Classification Search ..... Plt./287, Plt./292

See application file for complete search history.

*Primary Examiner* — June Hwu

(74) *Attorney, Agent, or Firm* — C. A. Whealy

(57) ABSTRACT

A new and distinct cultivar of *Chrysanthemum* plant named 'Mefisto Purple', characterized by its compact, upright, outwardly spreading and rounded plant habit; freely branching habit; dense and full plant habit; uniform and freely flowering habit; and decorative-type inflorescences with red purple-colored ray florets.

1 Drawing Sheet

Botanical designation: *Chrysanthemum×morifolium.*
Cultivar denomination: 'MEFISTO PURPLE'.

BACKGROUND OF THE INVENTION

The present invention relates to a new and distinct cultivar of *Chrysanthemum* plant, botanically known as *Chrysanthemum×morifolium*, and hereinafter referred to by the name 'Mefisto Purple'.

The new *Chrysanthemum* plant is a product of a planned breeding program conducted by the Inventor in Oostnieuwkerke, Belgium. The objective of the breeding program is to create new freely flowering *Chrysanthemum* plants with unique and attractive ray floret coloration.

The new *Chrysanthemum* plant originated from a cross-pollination made by the Inventor in Oostnieuwkerke, Belgium in October, 2005 of *Chrysanthemum×morifolium* 'Marenco Purple', not patented, as the female, or seed, parent with *Chrysanthemum×morifolium* 'Gedi One Car', disclosed in U.S. Plant Pat. No. 13,794. The new *Chrysanthemum* plant was discovered and selected by the Inventor as a flowering plant from within the progeny of the stated cross-pollination in a controlled greenhouse environment in Oostnieuwkerke, Belgium in October, 2006.

Asexual reproduction of the new *Chrysanthemum* plant by vegetative cuttings was first conducted in a controlled greenhouse environment in Oostnieuwkerke, Belgium in January, 2007. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Mefisto Purple'. These characteristics in combination distinguish 'Mefisto Purple' as a new and distinct *Chrysanthemum* cultivar:

1. Compact, upright, outwardly spreading and rounded plant habit.
2. Freely branching habit; dense and full plant habit.
3. Uniform and freely flowering habit.
4. Decorative-type inflorescences with red purple-colored ray florets.

Plants of the new *Chrysanthemum* differ from the female parent, 'Marenco Purple', in the following characteristics:

1. Plants of the new *Chrysanthemum* are more vigorous and larger than plants of 'Marenco Purple'.
2. Plants of the new *Chrysanthemum* have darker green-colored leaves than plants of 'Marenco Purple'.
3. Plants of the new *Chrysanthemum* and 'Marenco Purple' differ in ray floret color as plants of 'Marenco Purple' have darker-colored ray florets.

Plants of the new *Chrysanthemum* differ from the male parent, 'Gedi One Car', in the following characteristics:

1. Plants of the new *Chrysanthemum* flower later than plants of 'Gedi One Car'.
2. Plants of the new *Chrysanthemum* have larger inflorescences than plants of 'Gedi One Car'.
3. Plants of the new Chrysanthemum and 'Gedi One Car' differ in ray floret color as plants of 'Gedi One Car' have darker-colored ray florets.

Plants of the new *Chrysanthemum* can be compared to plants of *Chrysanthemum×morifolium* 'Contessa Lilac', not patented. In side-by-side comparisons conducted in Oostnieuwkerke, Belgium, plants of the new *Chrysanthemum* differed from plants of 'Contessa Lilac' in the following characteristics:

1. Plants of the new *Chrysanthemum* were not as vigorous as plants of 'Contessa Lilac'.
2. Plants of the new *Chrysanthemum* had larger inflorescences than plants of 'Contessa Lilac'.
3. Ray florets of plants of the new *Chrysanthemum* were flat and oval in shape whereas ray florets of plants of 'Contessa Lilac' were fused and tubular in shape.

BRIEF DESCRIPTION OF THE PHOTOGRAPH

The accompanying photograph illustrates the overall appearance of the new *Chrysanthemum* plant. This photograph shows the colors as true as it is reasonably possible to obtain in colored reproductions of this type. Colors in the photograph may differ slightly from the color values cited in the detailed botanical description which accurately describe the colors of the new *Chrysanthemum* plant. The photograph comprises a side perspective view of a typical flowering plant of 'Mefisto Purple' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn under conditions and practices which approximate those generally used in commercial production. During the production of the plants, day temperatures ranged from 25° C. to 30° C. and night temperatures ranged from 15° C. to 20° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Mefisto Purple'.

Parentage:

*Female, or seed, parent.*—*Chrysanthemum×morifolium* 'Marenco Purple', not patented.

*Male, or pollen, parent.*—*Chrysanthemum×morifolium* 'Gedi One Car', disclosed in U.S. Plant Pat. No. 13,794.

Propagation:

*Type.*—Terminal vegetative cuttings.

*Time to initiate roots, summer.*—About 14 days at temperatures of about 20° C.

*Time to initiate roots, winter.*—About 20 days at temperatures of about 20° C.

*Time to produce a rooted young plant, summer.*—About 30 days at temperatures of about 20° C.

*Time to produce a rooted young plant, winter.*—About 40 days at temperatures of about 20° C.

*Root description.*—Fine, fibrous; light brown in color.

*Rooting habit.*—Freely branching; moderately dense.

Plant description:

*Appearance.*—Perennial decorative-type *Chrysanthemum*; compact plant habit with stems upright and outwardly spreading giving a uniformly rounded appearance to the plant; very freely branching habit, about 25 primary lateral branches develop, each primary lateral branch with multiple secondary branches; pinching enhances lateral branch development; dense and full plant habit; strong and moderately vigorous growth habit.

*Plant height.*—About 40 cm.

*Plant width.*—About 60 cm.

*Lateral branches.*—Length: About 25 cm. Diameter: About 2 mm to 3 mm. Internode length: About 2 cm. Strength: Strong. Texture: Pubescent; longitudinally ridged. Color: Close to 144A.

*Leaves.*—Arrangement: Alternate, simple. Length: About 2.5 cm to 5 cm. Width: About 1.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Color: Developing leaves, upper surface: Close to 137C. Developing leaves, lower surface: Close to 137D. Fully expanded leaves, upper surface: Close to N137C; venation, close to 148C. Fully expanded leaves, lower surface: Close to 147B; venation, close to 147B to 147C. Petiole: Length: About 1 cm. Diameter: About 2 mm. Texture, upper and lower surfaces: Slightly pubescent and rough. Color, upper surface: Close to 146C. Color, lower surface: Close to 146D.

Inflorescence description:

*Appearance.*—Decorative-type inflorescence form; inflorescences borne on terminals above foliage; disc and ray florets arranged acropetally on a capitulum.

*Fragrance.*—Faintly fragrant, pungent.

*Flowering response.*—Under natural season conditions, plants flower mid-October in Belgium.

*Postproduction longevity.*—Inflorescences maintain good color and substance for about 35 days in an outdoor nursery; inflorescences persistent.

*Quantity of inflorescences.*—About 20 inflorescences develop per lateral branch.

*Inflorescence bud.*—Height: About 4 mm. Diameter: About 7 mm. Shape: Globular. Color: Between 144A and 137C.

*Inflorescence size.*—Diameter: About 4.5 cm. Depth (height): About 2.5 cm. Disc diameter: About 1 mm. Receptacle diameter: About 3 mm. Receptacle height: About 2.5 mm to 3 mm. Receptacle color: Close to 144B.

*Ray florets.*—Length: About 1.3 cm to 2 cm. Width: About 7 mm. Shape: Oval. Apex: Rounded. Base: Attenuate. Margin: Entire. Aspect: Mostly flat. Texture, upper and lower surfaces: Smooth, glabrous. Number of ray florets per inflorescence: About 200 arranged in about ten whorls. Color: When opening, upper and lower surfaces: Close to 72B. Fully opened, upper surface: Close to N74A; color becoming closer to N74B with development. Fully opened, lower surface: Close to 73A; color becoming closer to N74C with development.

*Disc florets.*—Length: About 3 mm. Diameter: About 0.5 mm to 1 mm. Shape: Tubular, elongated; apices acute. Number of disc florets per inflorescence: About 20. Color: Apex: Close to 144C. Mid-section: Close to 5B. Base: Close to 145D.

*Phyllaries.*—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles.*—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Color: Close to 146B.

*Reproductive organs.*—Androecium: Not observed. Gynoecium: Not observed.

*Seed/fruit.*—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Mefisto Purple' as illustrated and described.

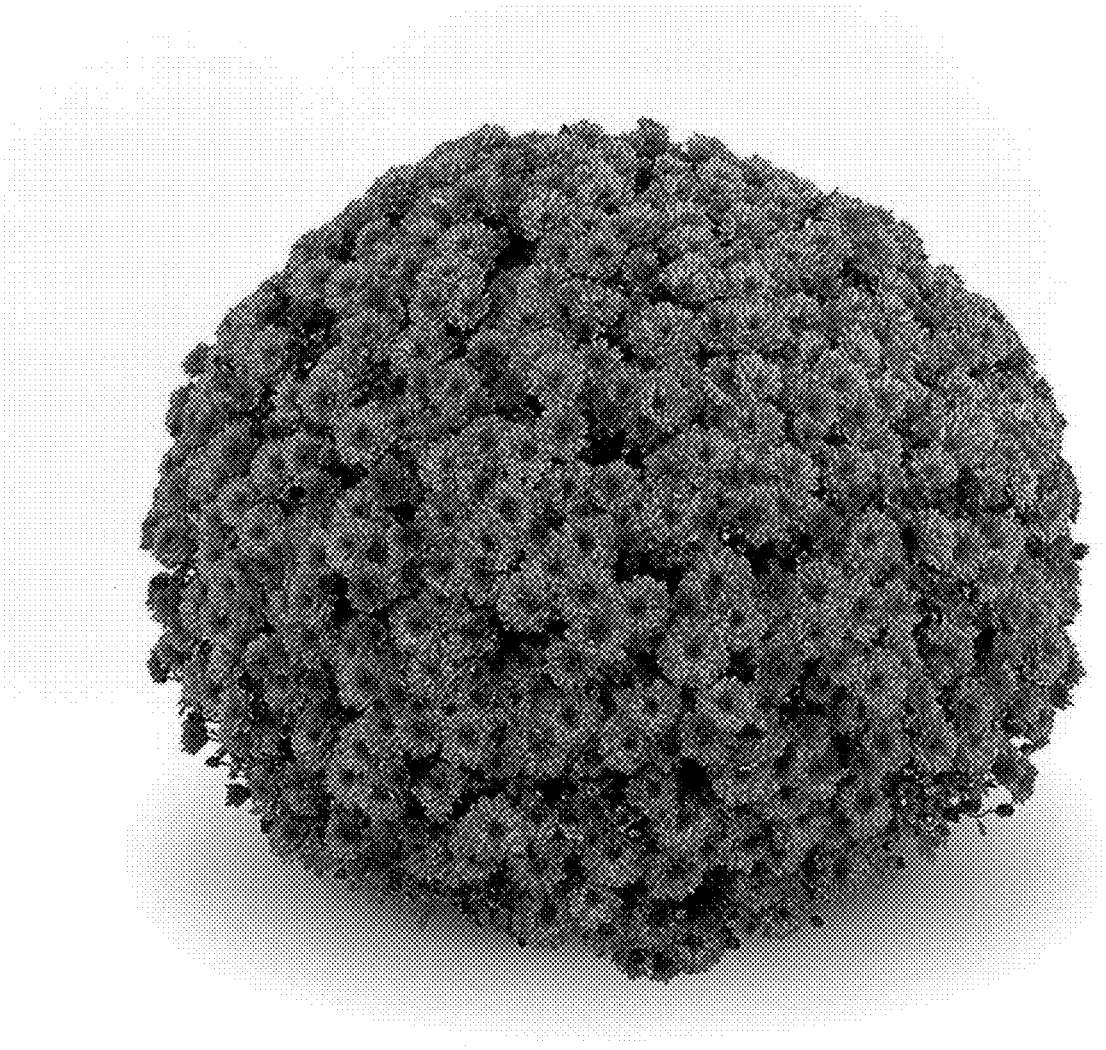

* * * * *